(12) United States Patent
Park et al.

(10) Patent No.: US 11,406,680 B2
(45) Date of Patent: Aug. 9, 2022

(54) HEALTH FUNCTIONAL FOOD FOR INHIBITING RISE OF BLOOD GLUCOSE CONTAINING COFFEE AND TAGATOSE

(71) Applicant: CJ CHEILJEDANG CORPORATION, Seoul (KR)

(72) Inventors: Byung Gyu Park, Suwon-si (KR); Young Mi Lee, Suwon-si (KR); Seong Bo Kim, Seongnam-si (KR); Seung Won Park, Yongin-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/931,662

(22) Filed: Jul. 17, 2020

(65) Prior Publication Data

US 2020/0360458 A1    Nov. 19, 2020

Related U.S. Application Data

(62) Division of application No. 16/096,949, filed as application No. PCT/KR2017/004717 on May 4, 2017, now abandoned.

(30) Foreign Application Priority Data

May 4, 2016 (KR) .......................... 10-2016-0055307

(51) Int. Cl.
| | |
|---|---|
| *A61K 36/74* | (2006.01) |
| *A23F 5/40* | (2006.01) |
| *A23L 2/60* | (2006.01) |
| *A23F 5/36* | (2006.01) |
| *A23F 5/42* | (2006.01) |
| *A61K 31/7004* | (2006.01) |

(52) U.S. Cl.
CPC ................ *A61K 36/74* (2013.01); *A23F 5/36* (2013.01); *A23F 5/40* (2013.01); *A23F 5/42* (2013.01); *A23L 2/60* (2013.01); *A61K 31/7004* (2013.01)

(58) Field of Classification Search
None
See application file for complete search history.

(56) References Cited

U.S. PATENT DOCUMENTS

| | | | |
|---|---|---|---|
| 9,879,296 B2 | 1/2018 | Lee et al. | |
| 10,039,834 B2 | 8/2018 | Prakash et al. | |
| 2001/0002269 A1 | 5/2001 | Zhao | |
| 2012/0207910 A1 | 8/2012 | Lee et al. | |
| 2014/0004244 A1 | 1/2014 | Putter et al. | |
| 2014/0010939 A1 | 1/2014 | Krohn | |
| 2014/0349950 A1 | 11/2014 | Kim et al. | |
| 2015/0018432 A1 | 1/2015 | Prakash et al. | |
| 2016/0192692 A1 | 7/2016 | Lee et al. | |
| 2016/0263170 A1* | 9/2016 | Turner | A61K 8/9717 |
| 2016/0346305 A1 | 12/2016 | Kim et al. | |
| 2017/0002391 A1 | 1/2017 | Lee et al. | |
| 2018/0296678 A1 | 10/2018 | Prakash et al. | |
| 2020/0331958 A1* | 10/2020 | Prakash | A23L 2/60 |

FOREIGN PATENT DOCUMENTS

| | | |
|---|---|---|
| CN | 102595919 A | 7/2012 |
| CN | 102711492 A | 10/2012 |
| CN | 103619191 A | 3/2014 |
| CN | 104739848 A | 7/2015 |
| CN | 105530960 A | 4/2016 |
| EP | 2 494 872 A2 | 9/2012 |
| EP | 2 756 764 A2 | 7/2014 |
| JP | 2009261277 | 11/2009 |
| JP | 2009286703 A | 12/2009 |
| JP | 4771882 B2 | 9/2011 |
| JP | 2008-189638 A | 12/2012 |
| JP | 2013063947 A | 4/2013 |
| JP | 2014-526258 A | 10/2014 |
| JP | 2015533515 | 11/2015 |
| KR | 10-2006-0006353 A | 5/2007 |
| KR | 10-0779160 B1 | 11/2007 |
| KR | 10-2009-0087346 A | 9/2010 |
| KR | 10-0982012 B1 | 9/2010 |
| KR | 10-2011-0047976 A | 2/2014 |
| KR | 10-1488844 B1 | 2/2015 |
| KR | 10-2016-0025275 A | 3/2016 |
| WO | 99/34689 A1 | 7/1999 |
| WO | 2015037679 | 3/2015 |

OTHER PUBLICATIONS

Kang, S. et al. The Effects of Using Artrificial Sweeteners and Coffee Grounds in Chocolate Filling on Quality Characteristics and Glycemic Index. J Applied Biological Chemistry 57(4)307-312, 2014. (Year: 2014).*
Book: Sweeteners and Sugar Alternatives in Food Technology, edited by Helen Mitchell, Blackwell Publishing 2006. Chapter 14 Tagatose pp. 263-294. (Year: 2006).*
Harold McGee, "On Food and Cooking the Science and Lore of the Kitchen Completely Revised and Updated", Jan. 1, 2004, XP055756189.
Bar Albert, "D-Tagatose", Bioresco, Aug. 2, 2004, pp. 1-156, XP055646211, URL:https://acnfp.food.gov.uk/sites/default/files/mnt/drupal_data/sources/files/multimedia/pdfs/tagatoseapplicationdossier.pdf.
Korean Office Action for the counterpart KR application 10-2017-0056846 (including English translation).
English Translation of International Search Report dated Jul. 11, 2017 for the corresponding PCT application PCT/KR2017/004717.
Korean Office Action for the counterpart KR application 10-2017-0056846 dated Apr. 4, 2019.

(Continued)

*Primary Examiner* — Ralph J Gitomer

(74) *Attorney, Agent, or Firm* — Renner, Otto, Boisselle & Sklar, LLP

(57) ABSTRACT

The present invention relates to a health functional food for inhibiting a rise of blood glucose containing coffee and tagatose.

19 Claims, 3 Drawing Sheets

(56) References Cited

OTHER PUBLICATIONS

Byung-gyu Park et al., "D-Tagatose, a Functional Sweetener, Affects the Glucose Responses in Healthy Subjects", Journal of the Korean Society of Food Science and Nutrition, 2012, 371-372.
Kang, Suna et al., "The Effects of Using Artificial Sweeteners and Coffee Grounds in Chocolate Filling on Quality Characteristics and Glycemic Index", Journal of Applied Biological Chemistry, 2014, vol. 57, No. 4, pp. 307-312, XP55646146.
CJ Cheiljedang, Tagatose, Aug. 23, 2012, XP55646418 <URL: http://www.cjingredient.com/product/tagatose.asp>.
Y. Lu et al., "Tagatose, a new antidiabetic and obesity control drug", Diabetes, Obesity and Metabolism, 2008, vol. 10, pp. 109-134, XP55022445.
Extended European Search Report for corresponding Patent Application No. 17792923.9 dated Dec. 6, 2019.
Wikipedia page about Tagatose Dec. 31, 2019 (Year: 2019).
Choi J. et al. Sweetness Potency and Sweetness Synergism of Sweeteners in Milk and Coffee Systems. Food Research Int 7 4: 168-176, Aug. 2015. (Year: 2015).
Original and English Translation of Chinese Office Action issued for corresponding Chinese Application 201780027673.8, dated Feb. 15, 2022.

* cited by examiner

【Figure 1】
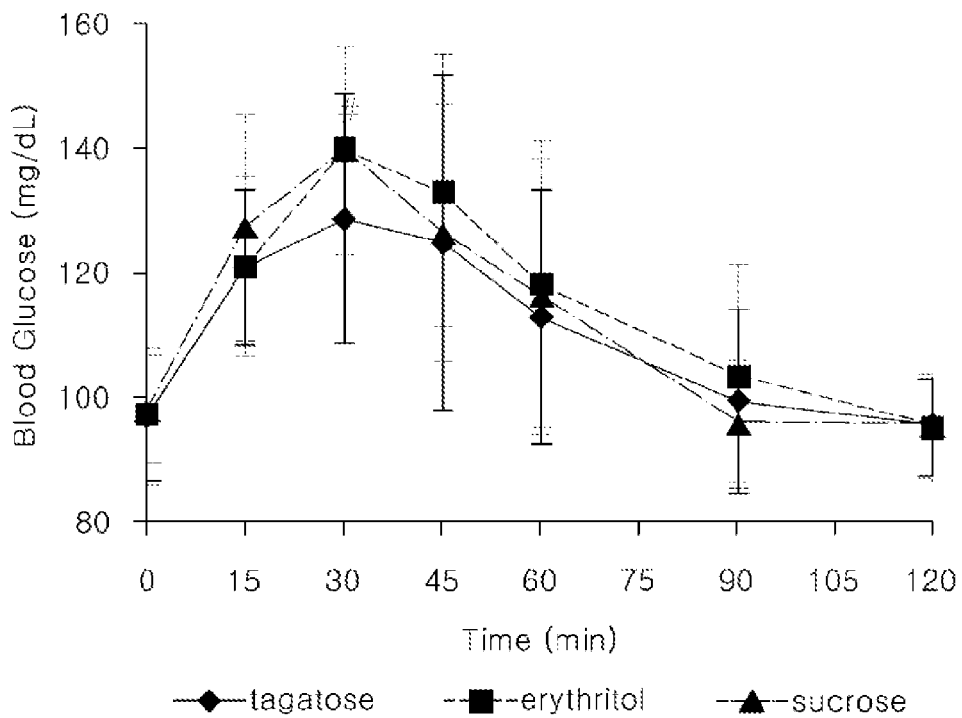
【Figure 2】
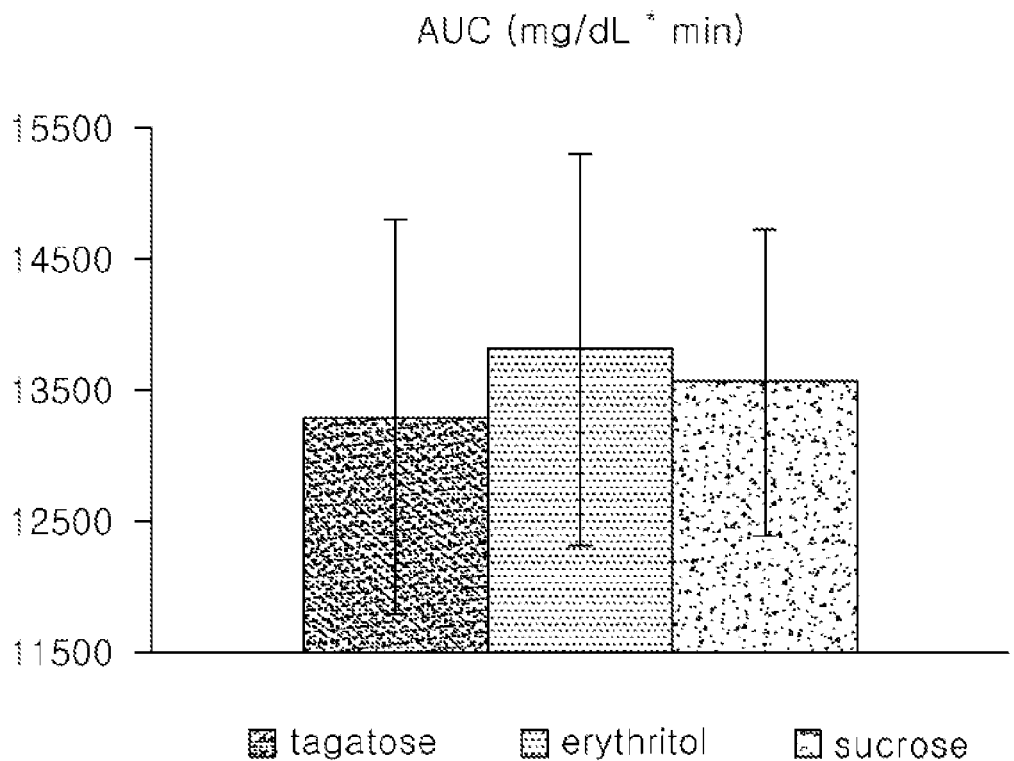

[Figure 3]
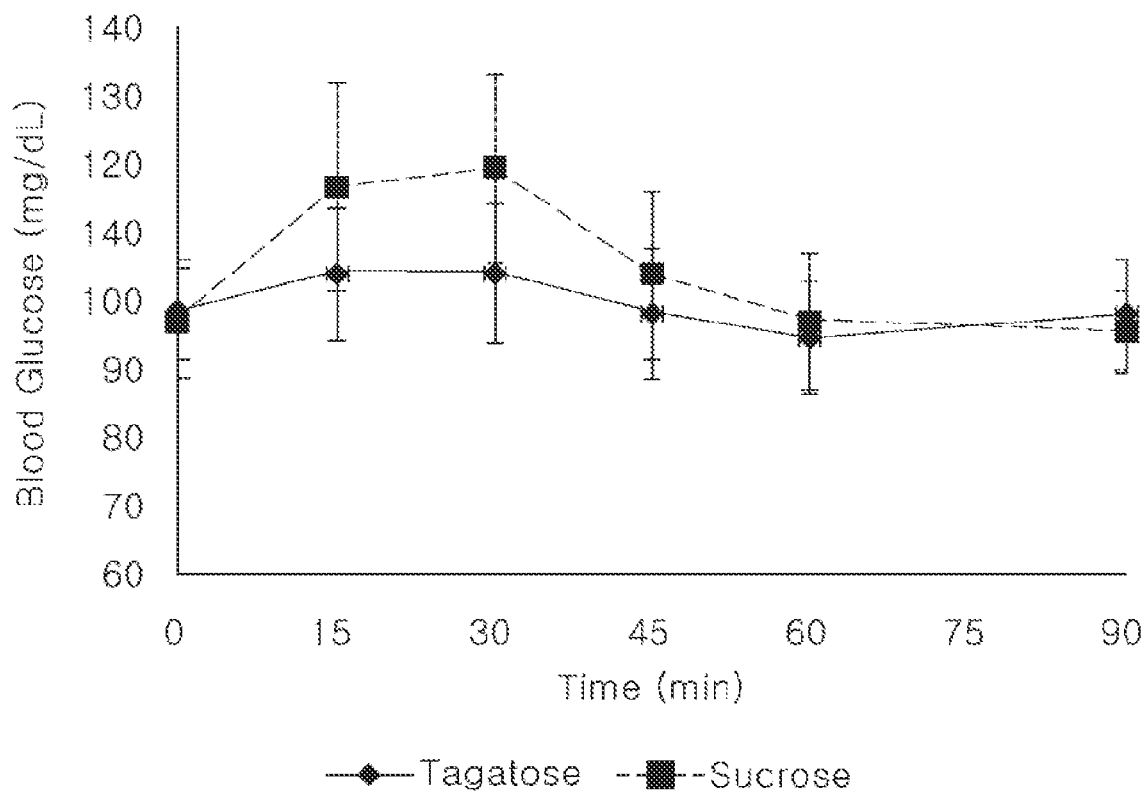
[Figure 4]
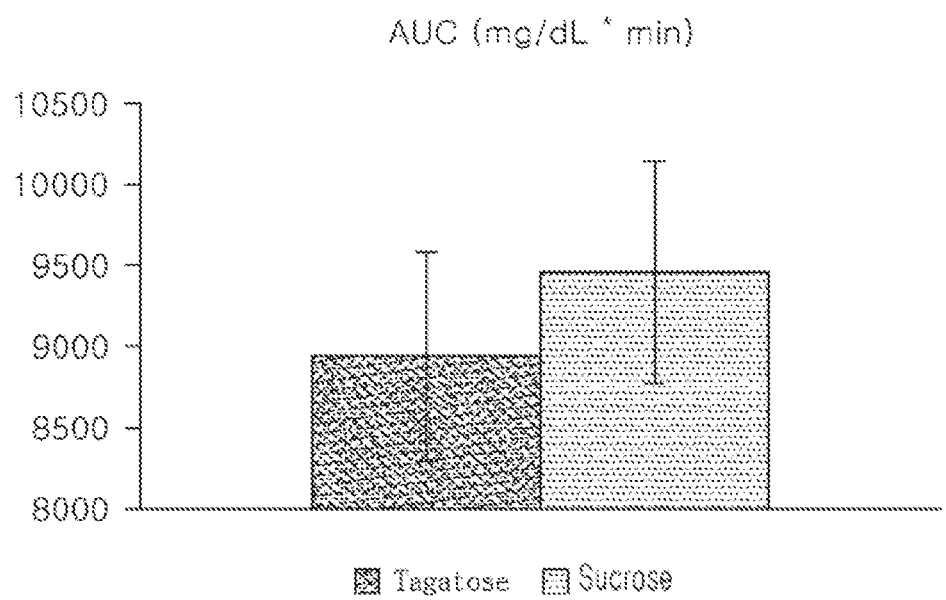

[Figure 5]
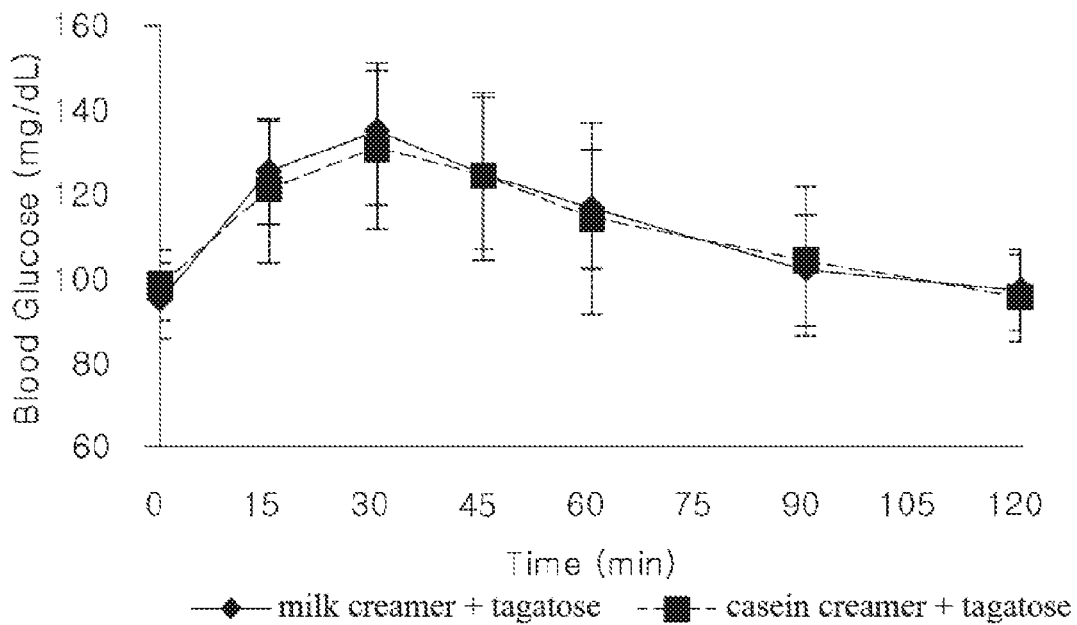
[Figure 6]
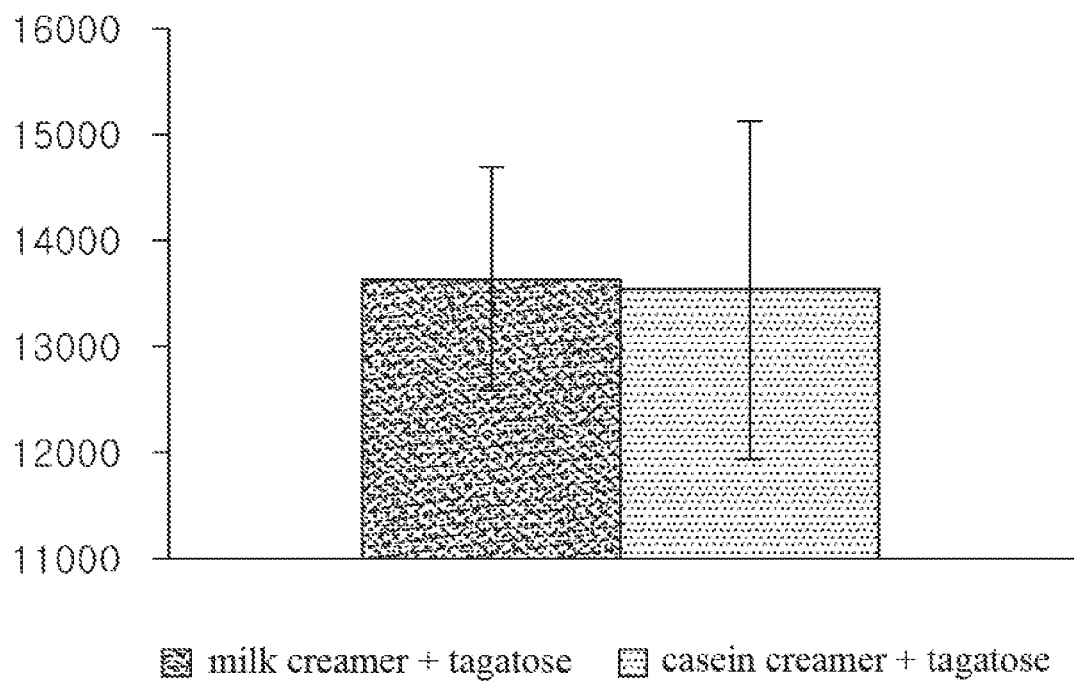

HEALTH FUNCTIONAL FOOD FOR INHIBITING RISE OF BLOOD GLUCOSE CONTAINING COFFEE AND TAGATOSE

This application is a divisional of U.S. patent application Ser. No. 16/096,949 filed Oct. 26, 2018 (now abandoned), which is a National Phase of International Patent Application No. PCT/KR2017/004717 filed May 4, 2017, which claims the benefit of and priority to Korean Patent Application No. 10-2016-0055307 filed on May 4, 2016, all of which are hereby incorporated herein by reference.

TECHNICAL FIELD

The present invention relates to a health functional food for inhibiting a rise in blood glucose, which includes coffee and tagatose.

BACKGROUND ART

Our human bodies require energy to maintain their own normal functions, and this energy is generated from nutrients in blood. Among the nutrients in blood, the most effective energy source is glucose which is a raw material important as an energy source for red blood cells and brain cells. Glucose in blood is referred to as blood glucose, and energy may be supplied to our bodies when the blood glucose always has to be maintained at a constant level. Particularly, a constant level of blood glucose is maintained by various hormones and enzymes. Insulin and glucagon are most representative of the hormones and enzymes. In this case, when ones do not eat food or require a large amount of energy, glucagon is secreted to help to release glucose, which has been stored in the liver, into blood so that the blood glucose can be maintained at a normal level. On the contrary, as a level of blood glucose increases after meal, insulin is secreted from the pancreas. In this case, insulin sends signals to store glucose in the liver, and promotes the use of glucose in cells of respective tissues to control a blood glucose level to a normal level.

In a normal state, blood glucose temporarily rises after meal, but returns to a normal level in response to insulin. However, when insulin is not normally secreted from the pancreas or insulin is secreted but does not function normally, the blood glucose does not return to a normal level after meal. That is, the bodies do not use glucose as energy source, thereby making impossible to excrete the glucose. When a level of blood glucose higher than a normal level lasts, it may interfere with regulatory components circulated through blood, reduce the functions of red and white blood cells, or put the pressure on the kidney, thereby negatively affecting our bodies.

As an isomer of galactose, tagatose is a naturally existing rare sucrose that is included as a trace element in foods such as dairy products, fruits, and the like, and has been registered as the FDA GRAS and EU Novel Food and approved to be safe by the Korea Food & Drug Administration (KFDA). Although the KFDA has approved tagatose as a raw material which help to inhibit a rise in blood glucose after meal, there is no report showing that the tagatose functions to inhibit a rise in blood glucose when taken with caffeine-containing coffee known to promote a rise in blood glucose after meal and taken with coffee (for example, a coffee mix) with a coffee creamer (glycemic index: 24) having a glycemic index (GI) higher than tagatose. Also, the patent (Registered Patent No. 10-1366404; Korean Patent Publication No. 2011-0047976) by the present inventors discloses a low-calorie coffee-mix composition in which tagatose is used instead of sucrose to make natural sweet tastes. However, there is no report on the coffee mix that functions to inhibit a rise in blood glucose.

In this context, the present inventors have ardently conducted research to confirm whether a tagatose coffee mix has an effect of inhibiting a rise in blood glucose, and found that the tagatose coffee mix has an excellent effect of inhibiting a rise in blood glucose, compared to the control and a sucrose coffee mix. Therefore, the present invention has been completed based on the facts.

DISCLOSURE

Technical Problem

Therefore, it is an object of the present invention to provide a health functional food for inhibiting a rise in blood glucose, which includes coffee and tagatose.

It is another object of the present invention to provide a method of inhibiting a rise in blood glucose, which includes administering the health functional food of the present invention to a subject in need thereof.

Technical Solution

To solve the above problems, according to an aspect of the present invention, there is provided a health functional food for inhibiting a rise in blood glucose, which includes coffee and tagatose.

The term "coffee" used herein refers to a powder of coffee obtained by roasting and grinding the fruit of a coffee tree, and includes a coffee been powder and instant black coffee, which are sold and distributed in various forms on the market, but the present invention is not limited thereto. Particularly, the coffee of the present invention may contain caffeine.

The term "tagatose" used herein refers to an isomer of galactose under the IUPAC name of (3S,4S,5R)-1,3,4,5,6-pentahydroxy-hexan-2-one. The tagatose of the present invention may be directly extracted from natural substances, and may be prepared using a chemical synthesis or biological method (for example, fermentation using microorganisms or enzymes), but the present invention is not limited thereto.

In the health functional food of the present invention, the tagatose of the present invention may be included at a dose of 6 g/day to 10 g/day. Particularly, the tagatose of the present invention may be included at a dose of 6 g/day to 7.5 g/day, 6 g/day to 7 g/day, 6 g/day to 6.5 g/day, or 6 g/day.

Also, the tagatose of the present invention may be provided in a crystalline form or in the form of a syrup containing tagatose. The tagatose-containing syrup may contain a varying amount of tagatose, based on the dried solid content (DS). Particularly, the tagatose of the present invention may be included at a tagatose content of 95% or more, and more particularly at a tagatose content of 96% or more, 97% or more, 98% or more, 99% or more, 99.5% or more, 99.5% to 99.9%, 99.5% to 99.8%, 99.5% to 99.7%, 99.5% to 99.6%, or 99.5%, based on the weight of dries solids. Also, the tagatose of the present invention may be in a crystalline form. When the tagatose of the present invention is used in a crystalline form, the tagatose may have any characteristics such as crystal morphology, particle size, crystal shape, or other physical characteristics in terms of the health functional food (for example, a health functional coffee mix) of the present invention.

Also, the health functional food of the present invention may further include a milk protein. The term "milk protein" used herein refers to a protein or derivatives thereof included in milk, and may be particularly selected from the group consisting of casein, sodium caseinate, a milk protein isolate, and a milk protein concentrate. More particularly, the milk protein of the present invention may be selected from the group consisting of casein, sodium caseinate, and a milk protein concentrate.

Also, the health functional food of the present invention may further include starch syrup. The term "starch syrup" used herein refers to a starch hydrolysate. Particularly, the starch syrup of the present invention may include maltose. More particularly, the starch syrup may include maltose and glucose and/or dextrin.

In the present invention, the inhibition of the rise in blood glucose may include a decrease in a blood glucose level by 3% to 20%, particularly by 3% to 15%, 3% to 10%, 3% to 7.6%, 3% to 6.35%, 5% to 20%, 5% to 15%, 5% to 10%, 5% to 7.6%, 5% to 6.35%, 6.35% to 7.6%, 6.35%, or 7.6% within 30 minutes to 45 minutes after the intake of the health functional food of the present invention relative to a blood glucose level of the control who does not eat the health functional food of the present invention.

Also, in the present invention, the inhibition of the rise in blood glucose may include a decrease in an area under the blood glucose response curve (AUC) by 2% to 10%, particularly by 2% to 7%, 2% to 5%, 2% to 3.8%, 3% to 10%, 3% to 7%, 3% to 5%, 3% to 3.8%, 3.8% to 10%, 3.8% to 7%, 3.8% to 5%, or 3.8% within 0 minutes to 120 minutes after the intake of the health functional food of the present invention relative to an area under the blood glucose response curve of the control who does not eat the health functional food of the present invention.

Meanwhile, in the present invention, the inhibition of the rise in blood glucose may include a decrease in a blood glucose level by 3% to 20%, particularly by 3% to 15%, 3% to 10%, 3% to 8%, 3% to 7.7%, 5% to 20%, 5% to 15%, 5% to 10%, 5% to 8%, 5% to 7.7%, 7% to 20%, 7% to 15%, 7% to 10%, 7% to 8%, 7% to 7.7%, or 7.7% within 30 minutes after the intake of the health functional food of the present invention relative to a blood glucose level of the control who eats tagatose instead of sucrose in the health functional food of the present invention.

Also, in the present invention, the inhibition of the rise in blood glucose may include a decrease in a blood glucose level by 3% to 20%, particularly by 3% to 15%, 3% to 13%, 3% to 12.7%, 3% to 11%, 3% to 10.8%, 5% to 20%, 5% to 15%, 5% to 13%, 5% to 12.7%, 5% to 11%, 5% to 10.8%, 8% to 20%, 8% to 15%, 8% to 13%, 8% to 12.7%, 8% to 11%, 8% to 10.8%, 10% to 20%, 10% to 15%, 10% to 13%, 10% to 12.7%, 10% to 11%, 10% to 10.8%, 10.8% to 20%, 10.8% to 15%, 10.8% to 13%, 10.8% to 12.7%, 12.7% to 20%, 12.7% to 15%, 12.7% to 13%, 10.8%, or 12.7% within 15 minutes to 30 minutes after the intake of the health functional food of the present invention relative to a blood glucose level of the control who eats sucrose instead of tagatose in the health functional food of the present invention.

In addition, in the present invention, the inhibition of the rise in blood glucose may include a decrease in an area under the blood glucose response curve by 2% to 10%, particularly by 2% to 8%, 2% to 6%, 2% to 5.49%, 3% to 10%, 3% to 8%, 3% to 6%, 3% to 5.49%, 5% to 10%, 5% to 8%, 5% to 6%, 5% to 5.49%, 5.49% to 10%, 5.49% to 8%, 5.49% to 6%, or 5.49% within 0 minutes to 90 minutes after the intake of the health functional food of the present invention relative to an area under the blood glucose response curve of the control who does not eat the health functional food of the present invention.

The food of the present invention may be used without limitation as long as it contains coffee and tagatose. Examples of the food of the present invention include bread, cake, chocolate, candies, confectionery (cookies, crackers, and the like), dairy products including ice creams, drinks and alcoholic beverages, and the like, the present invention is not limited thereto.

Particularly, the food of the present invention may be a coffee mix. The term "coffee mix" used herein refers to a food formulation which is packaged to include coffee as well as other additives (for example, a sweetener and/or a coffee creamer). The term "coffee creamer" used herein refers to an additive which serves to make coffee including a milk protein soft and rich in flavors, and may particularly further include starch syrup, and more particularly a vegetable oil, an emulsifying agent, a stabilizing agent and/or a buffer, all of which may be used for foods.

It is still another object of the present invention to provide a method of inhibiting a rise in blood glucose, which includes administering the health functional food of the present invention to a subject in need thereof.

In the method of inhibiting a rise in blood glucose according to the present invention, both of the health functional food of the present invention and the inhibition of the rise in blood glucose are applied as described above.

The term "administration" used herein refers to an introduction of a certain material to a subject of interest in any proper manner. In this case, the certain material may be administered through any general route of administration through which a composition of the present invention may reach an in vivo target. The routes of administration of the health functional food of the present invention are not particularly limited, but the health functional food of the present invention may be administered orally or parenterally. Particularly, the health functional food of the present invention may be administered orally. Also, the administration of the present invention may be performed so that the tagatose is included at a dose of 6 g/day to 10 g/day, 6 g/day to 7.5 g/day, 6 g/day to 7 g/day, 6 g/day to 6.5 g/day, or 6 g/day, based on the total weight of the health functional food of the present invention.

Those skilled in the art may recognize and appreciate the contents which are not described in this specification, and thus descriptions thereof will be omitted for clarity.

Advantageous Effects

According to the present invention, it has been clearly identified that a rise in blood glucose is inhibited even when tagatose is taken with caffeine-containing coffee and/or a coffee creamer having a high glycemic index (GI). As a result, it is expected that a food including coffee and tagatose will be used as a health functional food which help to inhibit a rise in blood glucose after meal.

DESCRIPTION OF DRAWINGS

FIG. 1 is a graph illustrating a change in blood glucose according to the intake of a coffee mix including tagatose, erythritol or sucrose according to one exemplary embodiment of the present invention.

FIG. 2 is a graph illustrating a change in an area under the blood glucose response curve (AUC) according to the intake of a coffee mix including tagatose, erythritol or sucrose according to one exemplary embodiment of the present invention.

FIG. 3 2 is a graph illustrating a change in blood glucose according to the intake of a coffee mix including tagatose or sucrose along with coffee and a coffee creamer according to one exemplary embodiment of the present invention.

from Dongsuh Food Co. Ltd.) and 6 g of coffee creamer 2 (a starch syrup including hydrogenated vegetable fats, non-fat milk, dibasic potassium phosphate, and a powder of milk protein concentrate; Namyang French Cafe Mix Creamer) to the coffee mix of Example 1, respectively. A coffee mix of Comparative Example 3 was prepared by replacing sucrose for only tagatose of Example 3.

TABLE 1

| Raw material | Relative degree of sweetness | Comparative Example 1 (g) | Comparative Example 2 (g) | Example 1 (g) | Example 2 (g) | Example 3 (g) | Comparative Example 3 (g) |
|---|---|---|---|---|---|---|---|
| Sucrose | 1 | 5 | — | — | — | — | 6 |
| Erythritol | 0.85 | — | 8.4 | — | — | — | — |
| Tagatose | 0.6 | — | — | 6 | 6 | 6 | — |
| Coffee | — | 1.6 | 1.6 | 1.6 | 1.6 | 1.6 | 1.6 |
| Coffee creamer 1 | — | — | — | — | 6 | — | — |
| Coffee creamer 2 | — | — | — | — | — | 6 | 6 |

FIG. 4 is a graph illustrating a change in an area under the blood glucose response curve according to the intake of a coffee mix including tagatose or sucrose along with coffee and a coffee creamer according to one exemplary embodiment of the present invention.

FIG. 5 is a graph illustrating a change in blood glucose according to milk proteins included in the coffee creamer according to one exemplary embodiment of the present invention.

FIG. 6 is a graph illustrating a change in in an area under the blood glucose response curve according to milk proteins included in the coffee creamer according to one exemplary embodiment of the present invention.

MODE FOR INVENTION

Hereinafter, the present invention will be described in detail with reference to exemplary embodiments thereof, but the present invention is not limited thereto. However, coffee mixes according to other examples than the embodiments will follow general technology known in the art. For example, see Korean Patent Publication No. 2011-0047976.

Preparative Example 1: Preparation of Coffee Mix

Coffee mixes were prepared as listed in the following Table 1.

Particularly, instant coffee (Maxim Mocha Gold Original, Dongsuh Food Co. Ltd.) was used as coffee in comparative examples and examples, and 6 g of tagatose (crystalline tagatose containing 98.5% tagatose, CJ CheilJedang Corp.) (Example 1), and 5 g of sucrose (white sucrose, CJ CheilJedang Corp.) (Comparative Example 1) and 8.4 g of erythritol (Zibo Zhongshi Green Biotech Co., Ltd) (Comparative Example 2) whose contents were adjusted to exhibit a degree of sweetness similar to that of the tagatose were used as a sweetener added to the coffee mixes in Comparative Examples 1 and 2 and Example 1. The erythritol was used as the placebo in Comparative Example 2 in which erythritol was added as a sweetening ingredient (0 Kcal, GI: 0) which had no effects on blood glucose.

Coffee mixes of Examples 2 and 3 were prepared by further adding 6 g of coffee creamer 1 (a starch syrup including hydrogenated vegetable fats, natural casein, dibasic potassium phosphate, and an emulsifying agent; 'Prima'

Experimental Example 1: Change in Blood Glucose According to Intake of Coffee Mix 1-1. Change in Blood Glucose According to Sweetener
1) Selection of Subjects and Intake Method To measure changes in blood glucose after the intake of the coffee mixes of Example 1 and Comparative Examples 1 and 2 prepared in Preparative Example 1, the following experiment was performed on 21 healthy persons (12 males and 9 females), with an average age of 32.4±5.5 years (between 25 and 42 years), who had a fasting blood sucrose level of 100 mg/dL or less.

Particularly, the subjects who had fasted since 10 p.m. the night before were randomly fed with muffin (a total of 326 kcal, including 19 g of sucrose) and the coffee mixes of Example 1 and Comparative Examples 1 and 2 (to perform randomization, double-blind, and cross-over tests).

2) Measurement of Changes in Blood Glucose and Area Under the Blood Glucose Response Curve To measure changes in blood glucose of subjects after meal, blood samples were taken through fingertip at time points of 0 minutes, 15 minutes, 30 minutes, 45 minutes, 60 minutes, 90 minutes, and 120 minutes after meal. Blood glucose contents were measured for every blood collection using an electrochemical method (Accu-Check, Roche). Area values under the blood glucose response curve (AUC) with the lapse of time were statistically processed based on the Student's paired t-test. $P<0.05$ was set to be of statistical significance as a threshold value.

As a result, it was revealed that the tagatose-containing coffee mix of Example 1 exhibited a significant decrease in blood glucose by 7.6% within 30 minutes after meal and a decrease in blood glucose by 6.35% within 45 minutes after meal, and also exhibited a significant decrease in an area under the blood glucose response curve (AUC) by 3.8% within 120 minutes after meal, compared to the placebo of Comparative Example 2. Also, it was revealed that the tagatose-containing coffee mix of Example 1 exhibited a significant decrease (7.7%) within 30 minutes after meal, compared to the sucrose-containing coffee mix of Comparative Example 1 (FIGS. 1 and 2). That is, it can be seen that the rise in blood glucose after meal was significantly inhibited when the caffeine-containing coffee and the tagatose-containing coffee mix were taken at a dose of 6 g/day after meal, and that the rise in blood glucose after meal was significantly inhibited even when compared to the existing commercial product, that is, a sucrose-containing coffee mix.

1-2. Change in Blood Glucose According to Intake of Coffee Creamer-Containing Coffee Mix 1) Selection of Subjects and Intake Method The following experiment was performed on 22 healthy persons (13 males and 9 females), with an average age of 32.4±5.5 years (between 25 and 42 years), who had a fasting blood sucrose level of 100 mg/dL or less.

Particularly, the subjects who had fasted since 10 p.m. the night before were randomly fed with the coffee mixes of Example 3 and Comparative Example 3 prepared in Preparative Example 1 (to perform randomization, double-blind, and cross-over tests).

2) Measurement of Changes in Blood Glucose and Area Under the Blood Glucose Response Curve Measurements of a change in blood glucose and an area under the blood glucose response curve for the subjects, and statistical processing were performed in the same manner as in Experimental Example 1-1. In the case of the change in blood glucose, the rises in blood glucose were significantly inhibited within 15 minutes (10.8%) and 30 minutes (12.7%) when the coffee mix containing tagatose and a coffee creamer (Example 3) was ingested, compared to when the coffee mix containing sucrose and a coffee creamer (Comparative Example 3) was ingested, and that the area under the blood glucose response curve (AUC) was also significantly inhibited by 5.49% within 90 minutes (FIGS. 3 and 4). Therefore, it can be seen that the rise in blood glucose after meal was significantly inhibited when the caffeine-containing coffee and the tagatose-containing coffee mix including a coffee creamer having a high GI were taken at a dose of 6 g/day or more, compared to the existing commercial product, that is, a coffee mix containing sucrose and a coffee creamer.

Experimental Example 2: Change in Blood Glucose According to Type of Milk Proteins in Coffee Creamer The same subjects as in Experimental Example 1 were fed with the coffee mixes of Examples 2 and 3 in the same manner to check a change in blood glucose and a change in an area under the blood glucose response curve according to the type of milk proteins in a coffee creamer. Casein was included in the coffee creamer of Example 2, and a milk protein concentrate was included in the coffee creamer of Example 3.

As a result, it was confirmed that there were no changes in blood glucose and area under the blood glucose response curve according to the type of the coffee creamers, indicating that there was no difference in an inhibitory effect of tagatose on the rise in blood glucose according to the type of milk proteins (FIGS. 5 and 6).

The invention claimed is:

1. A method of inhibiting a rise in blood glucose in a person taking coffee after meal, comprising:
administering a food comprising coffee and tagatose to the person,
wherein the tagatose is administered at a dose of 6 g/day to 10 g/day.

2. A method of inhibiting a rise in blood glucose in a person, comprising:
administering a food comprising coffee, tagatose, and a milk protein to the person, wherein the tagatose is administered at a dose of 6 g/day to 10 g/day.

3. The method of claim 1, wherein the tagatose is provided in the form of a syrup containing tagatose wherein the syrup contains the tagatose at a content of 95% by weight or more, based on the weight of dried solids; or the tagatose is provided in the form of crystalline.

4. The method of claim 2, wherein the milk protein is selected from the group consisting of casein, sodium caseinate, a milk protein isolate, and a milk protein concentrate.

5. The method of claim 1, wherein the food further comprises starch syrup.

6. The method of claim 1, wherein the coffee contains caffeine.

7. The method of claim 1, wherein the inhibition of the rise in blood glucose comprises a decrease in a blood glucose level by 3% to 20% within 30 minutes to 45 minutes after the intake of the food relative to a blood glucose level of the control who does not eat the food.

8. The method of claim 1, wherein the inhibition of the rise in blood glucose comprises a decrease in an area under the blood glucose response curve (AUC) by 2% to 10% within 0 minutes to 120 minutes after the intake of the food relative to an area under the blood glucose response curve of the control who does not eat the food.

9. The method of claim 1, wherein the inhibition of the rise in blood glucose comprises a decrease in a blood glucose level by 3% to 20% within 30 minutes after the intake of the food relative to a blood glucose level of the control who eats sucrose instead of tagatose in the food.

10. The method of claim 2, wherein the inhibition of the rise in blood glucose comprises a decrease in a blood glucose level by 3% to 20% within 15 minutes to 30 minutes after the intake of the food relative to a blood glucose level of the control who eats sucrose instead of tagatose in the food.

11. The method of claim 2, wherein the inhibition of the rise in blood glucose comprises a decrease in an area under the blood glucose response curve by 2% to 10% within 0 minutes to 90 minutes after the intake of the food relative to an area under the blood glucose response curve of the control who does not eat the food.

12. The method of claim 1, wherein the food is health functional food or dietary supplement.

13. The method of claim 2, wherein the tagatose is provided in the form of a syrup containing tagatose wherein the syrup contains the tagatose at a content of 95% by weight or more, based on the weight of dried solids; or the tagatose is provided in the form of crystalline.

14. The method of claim 2, wherein the food further comprises starch syrup.

15. The method of claim 2, wherein the coffee contains caffeine.

16. The method of claim 2, wherein the inhibition of the rise in blood glucose comprises a decrease in a blood glucose level by 3% to 20% within 30 minutes to 45 minutes after the intake of the food relative to a blood glucose level of the control who does not eat the food.

17. The method of claim 2, wherein the inhibition of the rise in blood glucose comprises a decrease in an area under the blood glucose response curve (AUC) by 2% to 10% within 0 minutes to 120 minutes after the intake of the food relative to an area under the blood glucose response curve of the control who does not eat the food.

18. The method of claim 2, wherein the inhibition of the rise in blood glucose comprises a decrease in a blood glucose level by 3% to 20% within 30 minutes after the intake of the food relative to a blood glucose level of the control who eats sucrose instead of tagatose in the food.

19. The method of claim 2, wherein the food is health functional food or dietary supplement.

\* \* \* \* \*